(12) United States Patent  
Leonardi

(10) Patent No.: US 6,428,167 B1  
(45) Date of Patent: Aug. 6, 2002

(54) EYEWEAR WITH PONYTAIL HOLDER

(75) Inventor: Peter F. Leonardi, Gloversville, NY (US)

(73) Assignee: Halo Sports and Safety, Inc., Gloversville, NY (US)

( * ) Notice: Subject to any disclaimer, the term of this patent is extended or adjusted under 35 U.S.C. 154(b) by 0 days.

(21) Appl. No.: 09/970,654

(22) Filed: Oct. 5, 2001

(51) Int. Cl.⁷ .................................................. G02C 3/00
(52) U.S. Cl. ........................ 351/157; 351/158; 132/273
(58) Field of Search ................................ 351/156, 157, 351/158, 52; 2/171, 209.3, 452; 132/273, 275

(56) References Cited

U.S. PATENT DOCUMENTS

| | | | |
|---|---|---|---|
| 2,648,255 A | 8/1953 | Pendleton | 351/156 |
| D171,056 S | 12/1953 | Schiaparelli | D57/1 |
| 3,038,376 A | 6/1962 | Kancepolsky | 351/156 |
| 3,173,147 A * | 3/1965 | Gross et al. | 351/156 |
| 4,712,254 A | 12/1987 | Daigle | 2/452 |
| 4,998,544 A | 3/1991 | Obergfell | 132/212 |
| 5,046,200 A * | 9/1991 | Feder | 2/452 |
| 5,495,623 A | 3/1996 | Leonardi | 2/431 |
| 5,546,603 A | 8/1996 | Lawhorne et al. | 2/181 |
| 5,555,571 A | 9/1996 | McCaffrey | 2/428 |
| 5,615,414 A | 4/1997 | Landis | 2/12 |
| 5,642,178 A | 6/1997 | Leonardi et al. | 351/111 |
| 5,644,799 A | 7/1997 | Armenta et al. | 2/209.3 |
| 5,644,800 A | 7/1997 | Leonardi | 2/431 |
| 5,875,488 A | 3/1999 | Milani | 2/12 |
| 5,969,788 A * | 10/1999 | Largura | 351/158 |

* cited by examiner

Primary Examiner—Huy Mai
(74) Attorney, Agent, or Firm—Roylance, Abrams, Berdo & Goodman, L.L.P.

(57) ABSTRACT

Eyewear including an eyewear frame with a first strap coupled thereto, and a ponytail holder member coupled to the first strap. The eyewear frame has first and second opposing frame ends. The first strap has opposing first and second strap ends, the first strap end being engaged with the first frame end of the eyewear frame. The ponytail holder member has a main body with an aperture substantially centrally located therein, and a first slot disposed adjacent the aperture. The first slot receives the first strap at the second strap end.

22 Claims, 2 Drawing Sheets

EYEWEAR WITH PONYTAIL HOLDER

FIELD OF THE INVENTION

The present invention generally relates to protective eyewear used in sporting activities that includes a mechanism surrounding the ponytail of the wearer allowing proper position of the eyewear strap. More specifically, the eyewear includes a ponytail holder that is attached to the flexible strap of the eyewear.

BACKGROUND OF THE INVENTION

Conventional protective eyewear provides protection for the eyes of the wearer particularly during a sporting activity where injury to a person's eyes is increased. Specifically, conventional protective eyewear includes a semi-flexible eyewear frame that supports two lenses with a strap for supporting the eyewear on the wearer's head.

However, the straps of conventional protective eyewear are obstructed by the ponytail of the wearer, thereby by making it difficult to properly and securely position the strap and thus eyewear on the head of the wearer. Also, the strap of the conventional eyewear can force the ponytail out of place, causing the ponytail to fall down.

Additionally, some conventional headbands include either an aperture or a ring through which the ponytail of the wearer can extend. However, these headbands cannot support an eyewear frame and the ponytail holders cannot be adapted to conventional eyewear. Moreover, some of the ponytail holders of conventional headbands are not flexible and do not conform to the shape of the wearer's head, thereby making the headband less comfortable to the wearer.

Examples of conventional protective eyewear include U.S. Pat. No. 5,644,800 to Leonardi; U.S. Pat. No. 5,642,178 to Leonardi et al.; and U.S. Pat. No. 5,495,623 to Leonardi. Examples of conventional headbands with ponytail holders include U.S. Pat. No. 5,875,488 to Milani; U.S. Pat. No. 5,615,414 to Landis; U.S. Pat. No. 5,546,603 to Lawhome et al.; and U.S. Pat. No. 4,998,544 to Obergfell.

SUMMARY OF THE INVENTION

Accordingly, an object of the present invention is to provide eyewear with a ponytail holder that supplies protection for the wearer's eyes and surrounds rather than obstructs the wearer's ponytail.

Another object of the present invention is to provide eyewear with a ponytail holder that has sufficient flexibility to conform to the wearer's head, thereby providing a comfortable fit, and is also sufficiently rigid to surround the wearer's ponytail.

Yet another object of the present invention is to provide eyewear with a ponytail holder that is readily adaptable to any eyewear strap.

The foregoing objects are basically attained by eyewear, comprising an eyewear to eyewear frame that has first and second opposing frame ends; a first strap coupled to the eyewear frame and having opposing first and second strap ends, the first strap end being engaged with the first frame end of the eyewear frame; and a ponytail holder member coupled to the first strap and including a main body that has an aperture substantially centrally located therein, and a first slot disposed adjacent the aperture, the first slot receiving the first strap at said second strap end.

The foregoing objects are also attained by eyewear, comprising an eyewear frame that has first and second opposing frame ends; a flexible first strap coupled to the eyewear frame and having a substantially flexible portion, and opposing first and second strap ends, the first strap end being engaged with the first frame end of the eyewear frame; and a separable ponytail holder member coupled to the first strap and including a substantially planar main body with a central longitudinal axis and a transverse axis substantially perpendicular to the longitudinal axis, and an aperture substantially centrally located therein, whereby the ponytail holder member is substantially flexible along a plane defined by the longitudinal axis and is substantially rigid along a plane defined the transverse axis.

By designing the eyewear in this fashion, protection to the wearer's eyes is provided in addition to a comfortable and secure fit of the eyewear.

Other objects, advantages and salient features of the invention will become apparent from the following detailed description, which, taken in conjunction with annexed drawings, discloses a preferred embodiment of the present invention.

BRIEF DESCRIPTION OF THE DRAWINGS

Referring to the drawings which form a part of this original disclosure.

DETAILED DESCRIPTION OF THE INVENTION

Figure 1:
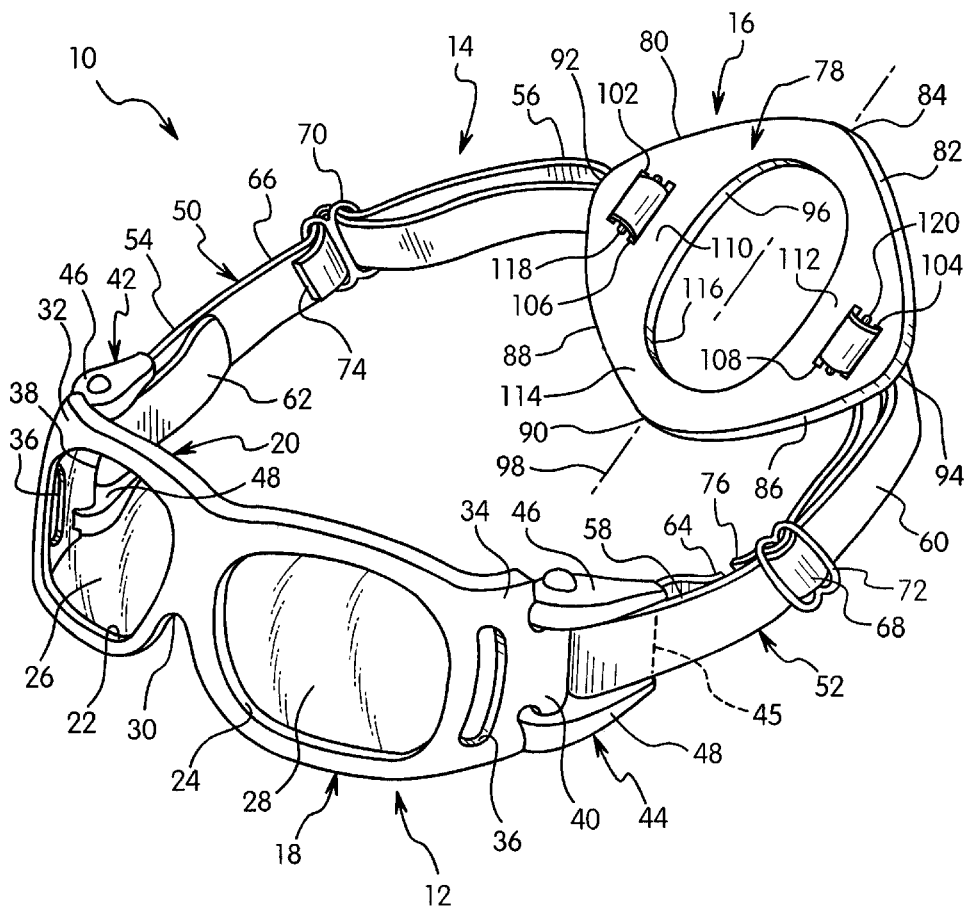
FIG. 1 is a perspective view of the eyewear in accordance with the present invention, showing an eyewear frame and strap, and a ponytail holder coupled to the strap.
Figure 2:
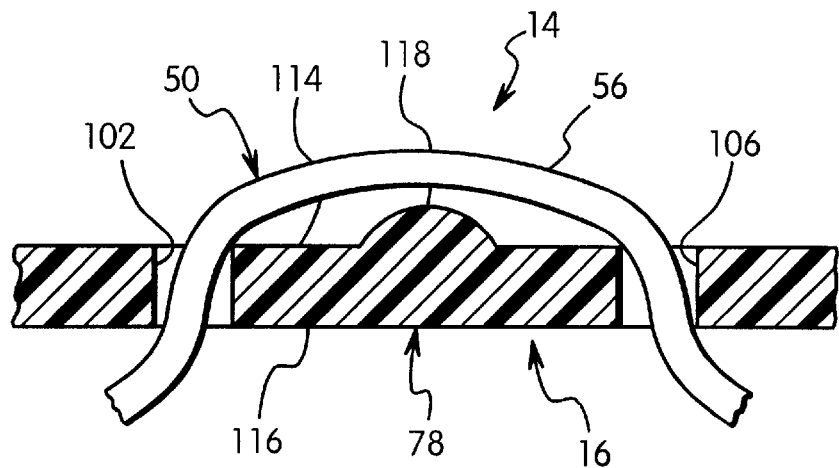
FIG. 2 is a partial sectional view of the ponytail holder and strap of the eyewear illustrated in FIG. 1, showing engagement of the strap and ponytail holder.
Figure 3:
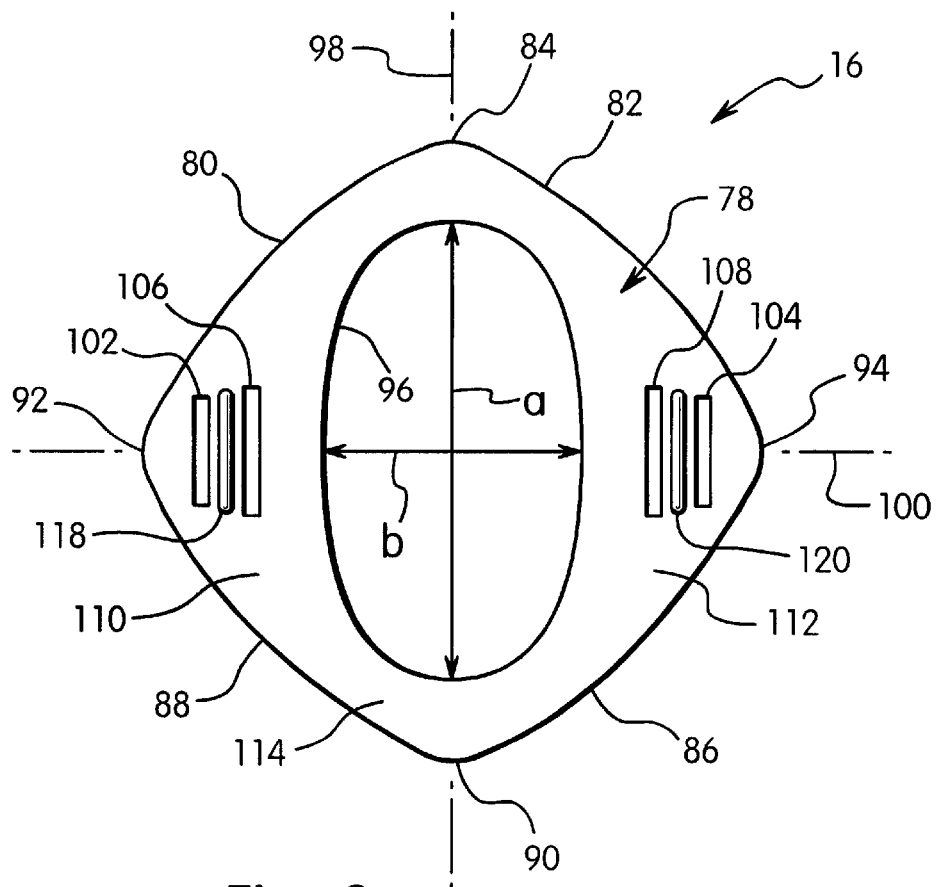
FIG. 3 is a front elevational view of the ponytail holder of the eyewear illustrated in FIG. 1.

Referring to FIGS. 1–3, eyewear 10 in accordance with the present invention generally includes eyewear or eyeglass frame 12 with a strap member 14 coupled thereto, and a ponytail holder member 16 coupled to strap member 14. Eyewear 10 provides protection for the wearer's eyes while not obstructing wearer's ponytail.

As seen in FIG. 1, eyewear frame 12 is of conventional design and is preferably substantially rigid so as to be generally shatterproof. For example, eyewear frame 12 can be formed of substantially rigid nylon. Frame 12 includes opposing front and rear portions 18 and 20 in between upper and lower edges, and first and second openings 22 and 24, which support first and second lenses 26 and 28. A nose area 30 is located between first and second openings 22 and 24.

First and second frame ends 32 and 34 extend outwardly from rear portion 20 of frame 12, thereby generally conforming to the shape of the wearer's head. Elongated openings 36 are located between first opening 22 and first end 32, and second opening 24 and second end 34, respectively. First and second hooks 38 and 40 extend from each of first and second frame ends 32 and 34.

Preferably, eyewear frame 12 is formed as a one-piece member but can be formed from separate components and integrally attached. Preferably, separate retaining members or strap connectors 42 and 44 are coupled to first and second frame ends 32 and 34, respectively, for releasably supporting strap member 14. Strap connectors 42 and 44 are disclosed in detail in U.S. Pat. No. 5,642,178 to Leonardi et al. entitled Sports Eyeweares With Soft, Resilient Connector Pads, the subject matter of which is hereby incorporated by reference.

In general, strap connectors 42 and 44 are flexible and preferably made of a rubber material. Each connector 42 and 44 includes a body 45 releasably coupled to strap member 14, and upper and lower arms 46 and 48 coupled to first and second hooks 38 and 40 of first and second frame ends 32 and 34, respectively.

As seen in FIGS. 1–2, strap member 14 is coupled to frame strap connectors 42 and 44, thereby allowing the wearer to secure eyewear 10 on the wearer's head. Strap member 14 is preferably made of a flexible, resilient, or elastic material. However, any material, such as a more rigid material, can be used for strap member 14 as long as strap member 14 supports eyewear frame 12 on the wearer's head. Additionally, strap member 14 can be any type of strap, band, or the like and can be directly coupled in a conventional manner to frame 12.

Strap member 14 specifically includes first and second straps 50 and 52. First strap 50 is coupled to frame first strap connector 42 at a first strap end 54 and is coupled to ponytail holder member 16 at a second strap end 56, as best seen in FIG. 1. Similarly, second strap 52 is coupled to frame second strap connector 44 at a first strap end 58 and is coupled to ponytail holder member 16 at a second strap end 60. Specifically, each of first strap ends 54 and 56 of both first and second straps 50 and 52 extends between the upper and lower arms 46 and 48 of frame first and second strap connectors 42 and 44, respectively. Also, the distal ends 62 and 64 of each first strap ends 54 and 56 are attached to each main portion 66 and 68 of each of first and second straps 50 and 52, respectively, by any attachment, such as sewing, hook and loop fasteners, or other conventional fasteners, thereby securely coupling first and second straps 50 and 52 to eyewear frame 12.

First and second buckles 70 and 72 are disposed on the main portions 66 and 68 of first and second straps 50 and 52, respectively. Buckles 70 and 72 are conventional buckles well known in the art. The distal ends 74 and 76 of second strap ends 56 and 60 also extend through buckles 70 and 72, respectively, thereby allowing first and second straps 50 and 52 to adjust in length to conform to the wearer's head by sliding each distal end 74 and 76 with respect to each strap main portion 66 and 68, respectively.

Although it is preferable to use buckles 70 and 72 for adjustability, they are not necessary. Additionally, a single unitary strap can be used instead of first and second straps 50 and 52, as long as the strap does not obstruct ponytail holder member 16.

Each of second strap ends 56 and 60 of first and second straps 50 and 52 engage ponytail holder member 16. Ponytail holder member 16 is sized and shaped to fit around the ponytail of the wearer thereby allowing strap member 14 to be properly positioned on the wearer's head instead of above or below the wearer's ponytail. As seen in FIGS. 1–3, ponytail holder member 16 generally includes a unitary main body 78 that is preferably substantially flat or planar and preferably made of polymeric material such as nylon. Main body 78 includes four sidewalls forming a generally square shape. However, main body 78 can be other shapes, such as any polygonal, annular, ring, or circular shape. First and second sidewalls 80 and 82 meet at a first junction point 84, and third and fourth sidewalls 86 and 88 meet at a second junction point 90. Similarly, first and fourth sidewalls 80 and 88 meet at a third junction point 92, and second and third sidewalls 82 and 86 meet at a fourth junction point 94. Both, the distance between first and second junction points 84 and 90 and the distance between third and fourth junction points 92 and 94 is preferably about 3 (three) inches. However, these distances and the size of main body 78 can be smaller or larger as desired.

An aperture 96 is substantially centrally disposed in main body 78 and is preferably oval in shape defining an elongated dimension "a" between first and second junction points 84 and 90 of main body 78, and a shortened dimension "b" between third and fourth junction points 92 and 94, as best seen in FIG. 3. Although it is preferable that aperture 96 is generally oval in shape, aperture 96 can be other shapes, such as any polygonal, annular, ring or circular shape. A central longitudinal axis 98 of main body 78 is defined along elongated dimension a, and a transverse axis 100 is defined along shortened dimension b.

Ponytail holder member 16 is thin and flat, and thus is substantially flexible and resilient about its central longitudinal axis 98 and transverse axis 100 to generally conform to the curvature of the wearer's head when eyewear 10 is place thereon. Ponytail holder member 16 is substantially rigid and resists tension forces outwardly away from longitudinal axis 98 and along the transverse axis 100, to provide sufficient rigidity to support the wearer's ponytail so that the ponytail is generally stabilized and not readily deformable. The same is true regarding tension forces along axis 98. In particular, substantially rigid means that main body 78 generally cannot be readily stretched or pulled outwardly along axes 98 and 100. Similarly, main body 78 cannot be readily pushed inwardly along axes 98 and 100. For example, if the sides of central aperture 96 where pulled outwardly during normal use, main body 78 would remain substantially in its original shape. Also, if the junction points 84, 90, 92, and 94 of main body 78 were pushed inwardly dining normal use, main body 78 would remain substantially in its original shape.

Main body 78 of ponytail holder member 16 includes first, second, third, and fourth slots 102, 104, 106, and 108, for receiving first and second straps 50 and 52. First and third slots 102 and 106 are disposed on one side 110 of main body 78 and second and fourth slots 104 and 108 are disposed on the opposite side 112 with central aperture 96 being located therebetween. All of slots 102, 104, 106, and 108 are substantially straight, and substantially parallel with and laterally spaced from central longitudinal axis 98. First and second slots 102 and 104 are proximate junction points 92 and 94 or main body 78, respectively, and farthest from central aperture 96. Third and fourth slots 106 and 108 are spaced from first and second slots 102 and 104, respectively, and are closest to central aperture 96.

First and second slots 102 and 104 are generally shorter in length than third and fourth slots 106 and 108 with first and second slots 102 and 104 being about 0.50 inches long and third and fourth slots 106 and 108 being about 0.675 inches long. However, the lengths of the slots can vary to accommodate different sized straps and each slot can either be the same or a different length than every other slot. Additionally, each slot 102, 104, 106, and 108 extends through from the first or front side 114 of main body 78 to the second or back side 116. Each of front and back sides 114 and 116 is substantially planar. The terms "front" and "back" are used only to facilitate description of ponytail holder member 16. Thus, first and second sides 114 and 116 could be either the front or back side, respectively.

A first rib 118 is located between and spaced from first and third slots 102 and 106, as seen in FIG. 2. Similarly a second rib 120 is located between and spaced from second and fourth slots 104 and 108. First and second ribs 118 and 120 are located on either the main body front side 114 or back side 116. First and second ribs 118 and 120 provide some rigidity to each space between first and third slots 102 and 106 and between second and fourth slots 104 and 108, respectively. Also, first and second ribs 118 and 120 provide additional securement for straps 50 and 52, particularly in maintaining straps 50 and 52 in place.

Assembly of eyewear 10 simply requires attaching the first strap ends 54 and 58 of strap member 14 to eyewear frame 12 at each of the strap connectors 42 and 44, respectively. Once eyewear frame 12 and strap member 14 are assembled, ponytail holder member 16 is coupled with strap member 14.

Specifically, each distal end 74 and 76 of first and second straps 50 and 52, respectively, are inserted through first and second slots 102 and 104 of ponytail holder member 16, preferably from the main body back side 116 through to the front side 114. Each of the strap distal ends 74 and 76 is extended over first and second ribs 118 and 120, respectively, and inserted into third and fourth slots 106 and 108, respectively, as seen in FIG. 2 (showing first and third slots 102 and 106 only). This leaves first and second straps 50 and 52 extending from the back side 116 of ponytail holder member 16. Each of the distal ends 74 and 76 can then be inserted into buckles 70 and 72, respectively, located on the main portions 66 and 68 of first and second straps 50 and 52, respectively, thereby securing ponytail holder member 16 to first and second straps 50 and 52. Alternatively, buckles 70 and 72 can be eliminated, thereby leaving strap distal ends 74 and 76 free.

Although it is preferable to insert the first and second strap distal ends 74 and 76 from the back side 116 of ponytail holder member 16, strap distal ends 74 and 76 can be inserted into the front side 114. As such, each distal end 74 and 76 would be inserted through first and second slots 102 and 104, respectively, then extended around the back side 116, and inserted into third and fourth slots 106 and 108, respectively. In this arrangement, since first and second ribs 118 and 120 are disposed on the ponytail holder member front side 114, strap distal ends 74 and 76 would not extend over ribs 118 and 120, respectively.

In use, the wear maneuvers their ponytail through aperture 96 of ponytail holder 16 and places the eyewear frame 12 over their eyes and supported on their nose. Since strap 14 is coupled to ponytail holder 16 and ponytail holder 16 surrounds the wearer's ponytail, strap 14 is properly positioned on the wearer's head to provide a comfortable and secure fit of eyewear 10. Specifically, strap 14 does not have to be located too high or above the wearer's ponytail, or similarly too low or below the wearer's ponytail. Additionally, the flexibility of ponytail holder 16 aids in maintaining the proper position and comfort to the wearer.

While a particular embodiment has been chosen to illustrate the invention, it will be understood by those skilled in the art that various changes and modifications can be made therein without departing from the scope of the invention as defined in the appended claims.

What is claimed is:

1. Eyewear, comprising:
   an eyewear frame having first and second opposing frame ends;
   a first strap coupled to said eyewear frame and having opposing first and second strap ends, said first strap end being engaged with said first frame end of said eyewear frame; and
   a ponytail holder member coupled to said first strap and including a main body having an aperture substantially centrally located therein, and a first slot disposed adjacent said aperture, said first slot receiving said first strap at said second strap end.

2. Eyewear according to claim 1, wherein
   said ponytail holder member includes a central longitudinal axis and a transverse axis substantially perpendicular to said longitudinal axis; and
   said ponytail holder member is substantially flexible about said longitudinal axis and said transverse axis; and
   said ponytail holder member is not readily deformable along said longitudinal axis and along said transverse axis.

3. Eyewear according to claim 2, wherein
   said first strap is formed of an elastic material; and
   said ponytail holder member is formed of nylon.

4. Eyewear according to claim 1, wherein
   said ponytail holder member is separable from said first strap.

5. Eyewear according to claim 1, wherein
   said ponytail holder member includes a first rib disposed proximate said first slot.

6. Eyewear according to claim 5, wherein
   said first rib is located between said aperture and said first slot.

7. Eyewear according to claim 1, wherein
   said aperture is substantially oval in shape defining an elongated dimension; and
   said elongated dimension defining a central longitudinal axis of said aperture.

8. Eyewear according to claim 7, wherein
   said first slot is spaced from and substantially parallel with said central longitudinal axis of said aperture.

9. Eyewear according to claim 8, wherein
   said ponytail holder member includes a first rib disposed proximate said first slot; and
   said first rib is spaced from and substantially parallel with said central longitudinal axis of said aperture.

10. Eyewear according to claim 1, wherein
    a second strap is coupled to said eyewear frame and includes opposing first and second strap ends; and
    said first strap end is engaged with said second frame end of said eyewear frame.

11. Eyewear according to claim 10, wherein
    a second slot is disposed adjacent said aperture of said ponytail holder member and opposite said first slot; and
    said second slot receives said second strap at said second strap end.

12. Eyewear according to claim 10, wherein
    said ponytail holder member includes a second rib disposed proximate said second slot.

13. Eyewear according to claim 12, wherein
    said second rib is located between said aperture and said second slot.

14. Eyewear according to claim 10, wherein
    said eyewear frame includes first and second retaining members coupled to said first and second frame ends, respectively; and
    each of said first and second retaining members are coupled to each of said first strap ends of said first and second straps, respectively.

15. Eyewear according to claim 10, wherein
    said ponytail holder member includes a third slot spaced from said first slot, and a fourth slot spaced from said second slot.

16. Eyewear, comprising:

an eyewear frame having first and second opposing frame ends;

a flexible first strap coupled to said eyewear frame and having a substantially flexible portion, and opposing first and second strap ends, said first strap end being engaged with said first frame end of said eyewear frame; and a separable ponytail holder member coupled to said first strap and including a substantially planar main body with a central longitudinal axis and a transverse axis substantially perpendicular to said longitudinal axis, and an aperture substantially centrally located therein, whereby said ponytail holder member is substantially flexible about said longitudinal axis and said transverse axis, and said ponytail holder member is not readily deformable along said longitudinal axis and along said transverse axis.

17. Eyewear according to claim 16, wherein said ponytail holder member includes a first slot space from said aperture, said first slot receiving said second strap end of said first strap.

18. Eyewear according to claim 17, wherein said ponytail holder member includes a first rib disposed adjacent to said first slot, and said first rib being located between said aperture and said first slot.

19. Eyewear according to claim 17, wherein said ponytail holder member includes a second slot spaced from said aperture and remote from said first slot for receiving a second strap.

20. Eyewear according to claim 19, wherein said ponytail holder member includes a second rib disposed adjacent to said second slot, and said second rib being located between said aperture and said second slot.

21. Eyewear according to claim 16, wherein said ponytail holder member is a one-piece unitary member.

22. Eyewear, comprising:

an eyewear frame having first and second opposing frame ends;

a flexible first strap coupled to said eyewear frame and having opposing first and second strap ends, said first strap end being engaged with said first frame end of said eyewear frame;

a flexible second strap coupled to said eyewear frame and having opposing first and second strap ends, said second strap end being engaged with said second frame end of said eyewear frame; and a separable ponytail holder member coupled to said first and second straps and including a substantially planar main body having an aperture substantially centrally located therein, and first and second slots disposed adjacent to said aperture with said first slot being remote from said second slot, said first slot receiving said second strap end of said first strap, and said second slot receiving said second strap end of said second strap.

* * * * *